United States Patent [19]  [11] 4,058,561
Klauke et al.  [45] Nov. 15, 1977

[54] 2-CHLOROMETHYLPHENYLCARBAMIC ACID FLUORIDE

[75] Inventors: Erich Klauke, Odenthal; Horst Jäger, Leverkusen, both of Germany

[73] Assignee: Bayer Aktiengesellschaft, Leverkusen, Germany

[21] Appl. No.: 651,995

[22] Filed: Jan. 23, 1976

[30] Foreign Application Priority Data

Feb. 12, 1975  Germany ............................ 2505714

[51] Int. Cl.$^2$ ..................... C07C 101/44; C07C 63/52
[52] U.S. Cl. .......................... 260/544 C; 260/239.3 T
[58] Field of Search ................................... 260/544 C

[56] References Cited

U.S. PATENT DOCUMENTS

| | | | |
|---|---|---|---|
| 2,974,163 | 3/1961 | Juban et al. | 260/544 C |
| 3,041,364 | 6/1962 | McShane et al. | 260/544 C |
| 3,262,974 | 7/1966 | Steggerd | 260/544 C |
| 3,518,293 | 6/1970 | Klauke et al. | 260/544 C |

OTHER PUBLICATIONS

Houben–Weyl, "Methoden Der. Organischem. Chemie.," Bank V/3, Halogerverbindugens, pp. 113–114, (1962).

*Primary Examiner*—Norman Morgenstern
*Attorney, Agent, or Firm*—Burgess, Dinklage & Sprung

[57] ABSTRACT

2-Chloromethylphenylcarbamic acid fluoride is prepared by reacting 2-chloromethylphenylisocyanate with anhydrous hydrofluoric acid. The product prepared can be reacted further with anhydrous hydrofluoric acid under pressure to prepare 2-aminodiphenylmethane-2'-carboxylic acid lactam.

1 Claim, No Drawings

2-CHLOROMETHYLPHENYLCARBAMIC ACID FLUORIDE

This invention relates to 2-chloromethylphenylcarbamic acid fluoride, a process for its preparation and its use for the preparation of 2-aminodiphenylmethane-2'-carboxylic acid lactam.

The preparation of certain arylcarbamic acid fluorides by addition of hydrogen fluoride to the corresponding isocyanates is known. Thus, Houben-Weyl, 4th Edition, Volume V/3 page 113 et seq., describes the preparation of, for example, phenylcarbamic acid fluoride by reaction of phenylisocyanate with hydrofluoric acid.

SUMMARY

It has now been found that 2-chloromethylphenylcarbamic acid fluoride can be obtained by reacting 2-chloromethylphenylisocyanate with anhydrous hydrofluoric acid.

DESCRIPTION

The fact that the reaction of 2-chloromethylphenylisocyanate with hydrofluoric acid leads, in such a simple manner and without side-reactions, to the corresponding stable carbamic acid fluoride, was surprising since in general it is known that compounds of the character of benzyl chloride react very vigorously with Friedel-Crafts catalysts to form polybenzyls (see Beilstein, E III 5, page 638).

In general, the procedure followed in the preparation of 2-chloromethylphenylcarbamic acid fluoride is that the anhydrous hydrofluoric acid is first charged in at temperatures of 0° to 10° C and then 1 mol of 2-chloromethylphenylisocyanate is added per 0.5 to 1 mol of hydrofluoric acid. After the material has been added, the temperature of the reaction mixture is in general allowed to rise slowly to room temperature and left there for a prolonged period of time, in general until the reaction mixture has crystallised completely. The crystals are covered once with petroleum ether and then sucked dry on a suction filter.

2-Chloromethylphenylisocyanate is known and is, for example, obtainable in good yield and high purity by side-chain chlorination of 2-tolylisocyanate (see Houben-Weyl, Methods of Organic Chemistry, 4th Edition, Volume V/3, page 746 (1968)).

Commercial grades of anhydrous hydrofluoric acid can be employed.

The 2-chloromethylphenylcarbamic acid fluoride obtained according to the invention has a melting point of 64° C. The IR spectrum shows a C=O band at 1,762 $cm^{-1}$ and characteristic N-H adsorptions at 3272 and 1525 $cm^{-1}$. The $^{19}F$ nuclear resonance spectrum shows a resonance at −71.3 ppm (measured against $CF_3COOH$ as the external standard). In the mass spectrum, the molecular peak appears at 187 m/e.

Further, it has been found that 2-chloromethylphenylcarbamic acid fluoride can be used in a technically advantageous manner for the preparation of 2-aminodiphenylmethane-2'-carboxylic acid lactam. For this, the procedure followed is generally that anhydrous hydrofluoric acid and 2-chloromethylphenylcarbamic acid fluoride, preferably dissolved in benzene, are reacted under pressure, for example by introducing the reactants into an autoclave at low temperatures and the autoclave is then sealed and warmed. In this reaction 2-chlormethyl-phenylcarbamic acid fluoride is generally employed in amounts of 0.1 to 0.2 mols, relative to hydrofluoric acid. Benzene is present in excess relative to 2-chlormethylphenylcarbamic acid fluoride employed, and in general molar ratios of carbamic acid fluoride to benzene of 1 : 2 − 5 are chosen. In general, the carbamic acid fluoride/benzene and the hydrofluoric acid are mixed at temperatures of 0° to 5° C, whilst the cyclysation reaction takes place at higher temperatures, for example at temperatures from room temperature to 180° C, temperatures of 40° to 120° C being advantageous. The reaction time is in general ¼ to 12 hours, reaction times of 1 to 2 hours being preferred. After the reaction has taken place, the hydrofluoric acid and benzene are distilled off in a manner which is in itself known and the residue which remains is washed with alkali metal hydroxide solution, generally potassium hydroxide, filtered and dried. 2-Aminodiphenylmethane-2'-carboxylic acid lactam, thus obtained, is a valuable starting material for the synthesis of a wide range of pharmaceutical compounds. Thus it is known, for example, that N-dialkyl-aminoalkyl derivatives of 2-aminodiphenylmethane-2'-carboxylic acid lactam have a good antispasmodic action (Journal of Medical Chemistry, Volume 8, page 76 (1965)).

In a particularly advantageous embodiment of the preparation of 2-aminodiphenylmethane-2'-carboxylic acid lactam, the 2-chloromethylphenylcarbamic acid fluoride is not isolated as such. Here, the procedure followed is that hydrofluoric acid, in amounts of 2 to 10 mols, is initially introduced into an autoclave at temperatures of −10 to +10° C and 2-chloromethylphenylisocyanate, dissolved in benzene, is added dropwise thereto. After completion of the addition, the reaction mixture is then warmed to higher temperatures, for example to temperatures of 20° to 180° C, preferably to 40° to 120° C. Hereupon, a pressure of 2 to 50 atmospheres gauge in general becomes established in the autoclave. After cooling, and releasing the pressure, hydrofluoric acid and benzene are distilled off under atmospheric pressure until the internal temperature reaches 50° C and the residue in the autoclave is poured onto ice. The product is washed with dilute alkali metal hydroxide solution, in general with aqueous potassium hydroxide solution, filtered off, rinsed thoroughly with water and dried. 2-Aminodiphenylmethane-2'-carboxylic acid lactam can thus be obtained in a technically advantageous manner in one step directly by the reaction of 2-chloromethylphenylisocyanate with hydrofluoric acid.

EXAMPLE 1

5 g of anhydrous hydrofluoric acid are initially introduced into a stirred vessel made of stainless steel and 41.5 g of 2-chloromethylphenylisocyanate are added dropwise at 0° to 10° C. The reaction mixture is allowed to warm to room temperature and is left to stand at this temperature overnight. The batch which has crystallised throughout is covered once with petroleum ether and the product is then sucked dry on a suction filter. Yield: 44 g (91% of theory), melting point: 64° C.

EXAMPLE 2

40 ml of anhydrous hydrofluoric acid are initially introduced into an autoclave and 41 g of 2-chlorophenylcarbamic acid fluoride dissolved in 68 g of benzene are added at 0° to 5° C. The autoclave is sealed and warmed to 100° C for 1 hour. Hydrofluoric acid and benzene are distilled off and the residue which remains is washed with aqueous potassium hydroxide solution, filtered and dried. 44 g (= 96% of theory) of 2-aminodiphenylmethane-2'-carboxylic acid lactam of melting point 193° – 196° C are thus obtained.

EXAMPLE 3

400 ml of anhydrous HF are initially introduced into a stainless steel autoclave, fitted with a stirrer, at about 0° C. A solution of 340 g of 2-chloromethylphenylisocyanate in 800 ml of benzene is added dropwise thereto over the course of 45 minutes, during which the temperature is allowed to rise to 15° C. After completion of the addition the mixture is stirred for a further 15 minutes and the autoclave is then sealed and heated to 100° C for 15 minutes. In the course thereof, the pressure assumes a value of about 16 atmospheres gauge. After cooling, and releasing the pressure, the mixture is distilled under atmospheric pressure until the internal temperature is 50° C, and the residue in the autoclave, while still liquid, is poured onto ice. The product is washed with dilute aqueous KOH, filtered off, rinsed thoroughly with water and dried.

Yield: 408 g (96.2% of theory) of 2-aminodiphenylmethane-2'-carboxylic acid lactam of melting point 196° – 199° C.

What is claimed is:

1. 2-chloromethylphenylcarbamic acid fluoride.

* * * * *